(12) United States Patent
Lihl et al.

(10) Patent No.: US 7,514,042 B2
(45) Date of Patent: Apr. 7, 2009

(54) DEVICE AND METHOD FOR RAPID TISSUE PREPARATIONS FOR HISTOLOGICAL INVESTIGATIONS

(75) Inventors: Reinhard Lihl, Vienna (AT); Hubert Goll, St. Pölten (AT); Ferdinand Pauliny, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 700 days.

(21) Appl. No.: 10/491,386

(22) PCT Filed: Oct. 2, 2002

(86) PCT No.: PCT/EP02/11079

§ 371 (c)(1), (2), (4) Date: Jan. 14, 2005

(87) PCT Pub. No.: WO03/031943

PCT Pub. Date: Apr. 17, 2003

(65) Prior Publication Data
US 2005/0118670 A1    Jun. 2, 2005

(30) Foreign Application Priority Data
Oct. 6, 2001    (DE) .............................. 101 49 345

(51) Int. Cl.
B01L 3/00    (2006.01)
(52) U.S. Cl. ....................................................... 422/99
(58) Field of Classification Search .................... 422/99
See application file for complete search history.

(56) References Cited

U.S. PATENT DOCUMENTS

| | | |
|---|---|---|
| 3,771,490 A | 11/1973 | Kinney |
| 4,141,312 A | 2/1979 | Louder |
| 4,651,671 A | 3/1987 | Pedersen |
| 4,738,824 A | 4/1988 | Takeuchi |
| 5,080,869 A | 1/1992 | McCormick |
| 5,560,956 A * | 10/1996 | Schmehl .................... 427/2.11 |
| 5,895,628 A | 4/1999 | Heid et al. |
| 6,017,435 A | 1/2000 | Hassard |
| 6,058,788 A | 5/2000 | Thiem et al. |
| 6,444,170 B1 | 9/2002 | Heid et al. |
| 2002/0098118 A1 | 7/2002 | Eckert et al. |

FOREIGN PATENT DOCUMENTS

| | | |
|---|---|---|
| DE | AS 1 007 083 | 10/1957 |
| DE | 44 00 815 A1 | 1/1994 |
| DE | 44 00 815 A1 | 7/1995 |
| DE | 196 47 662 C1 | 11/1996 |
| DE | 196 52 339 A1 | 12/1996 |

(Continued)

Primary Examiner—Walter D Griffin
Assistant Examiner—Bobby Ramdhanie
(74) Attorney, Agent, or Firm—Houston Eliseeva LLP

(57) ABSTRACT

The device (1) for fast tissue processing for histological examination consists of a housing (2) that is covered by a transparent hood (70). A baseplate (3) divides the device (1) into an upper part (4a) and a lower part (4b). Several process chambers that are served by a transport mechanism (6) with holders (40) for tissue specimens are provided for on the baseplate (3). At least one reservoir (74) is provided for in the lower part (4b) of the device, which has a flow connection to at least one process chamber. An operating panel (76) allows the user to enter the appropriate data.

17 Claims, 8 Drawing Sheets

FOREIGN PATENT DOCUMENTS

Figure 1:
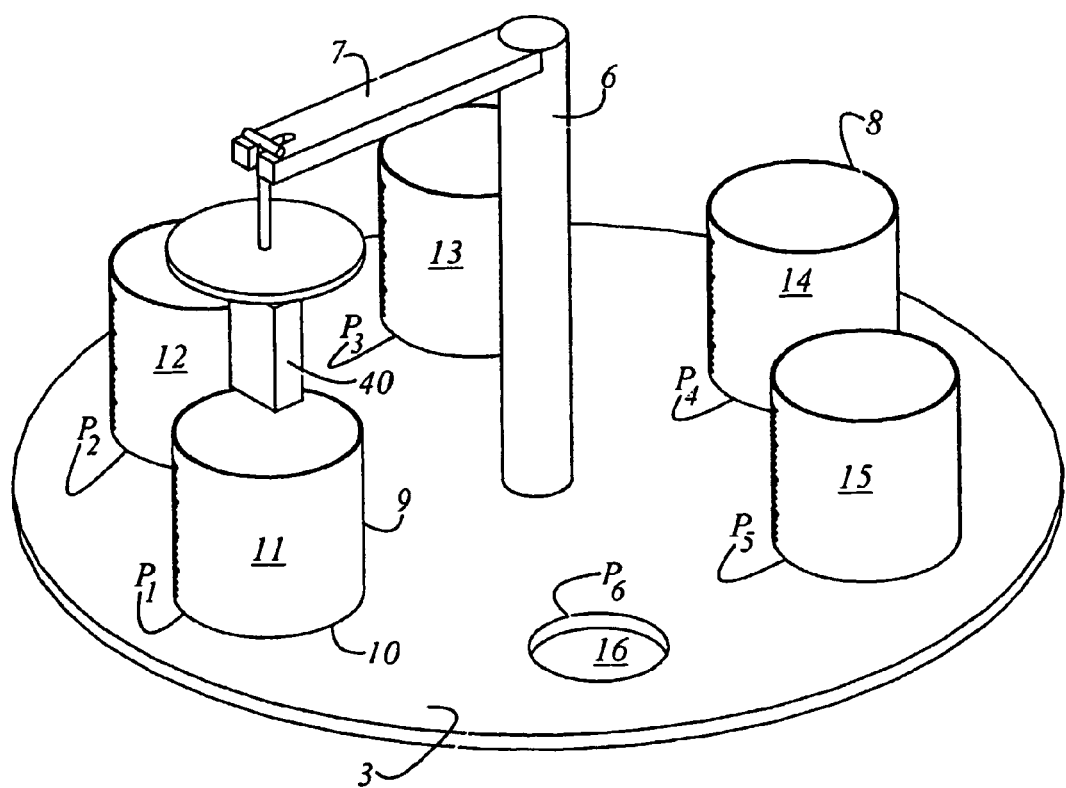

| | | |
|---|---|---|
| DE | 36 34 976 C2 | 9/1997 |
| EP | 0 269 316 B1 | 8/1994 |
| GB | 978 276 | 12/1964 |
| WO | WO 9920995 A1 * | 4/1999 |
| WO | WO 00/36393 A2 | 6/2000 |
| WO | WO 01/22 052 A1 | 3/2001 |
| WO | WO 01/44783 A1 | 6/2001 |
| WO | WO 02099429 A1 * | 12/2002 |

* cited by examiner

DEVICE AND METHOD FOR RAPID TISSUE PREPARATIONS FOR HISTOLOGICAL INVESTIGATIONS

The invention relates to a device for fast tissue processing for histological examinations, with a housing that is divided into an upper part and a lower part, several process chambers that are arranged on the baseplate, and a transport mechanism that transfers the tissue samples to the process chambers.

In addition, the invention relates to a method for fast tissue processing for histological examinations.

Document WO 01/44783 discloses a fast tissue processor. A microwave generator is attached to a reaction chamber for the tissue. The microwave generator produces warmth that allows the processes which the tissue samples undergo to run more quickly. For processing the tissue samples, several different modules that contain various liquids of varying composition are provided for. A disadvantage is that warming with microwaves may have an effect on the tissues being prepared.

U.S. Pat. No. 5,560,956 discloses a tissue processor that consists of numerous liquid reservoirs. The liquids in the reservoirs are pumped into a process chamber. After processing, the liquid is pumped back into the reservoir. A chamber for wax is also provided for. The preparation process provided for with this device takes approximately 8 to 12 hours, which cannot be considered a fast tissue processing.

Another tissue processor is disclosed in U.S. Pat. No. 3,771,490. Here, a sample chamber is provided for, into which the samples to be processed are placed. The various liquids are pumped into the sample chamber from chambers located beneath it. A disadvantage is that the various reagents must be introduced into a sample chamber, which leads to rapid contamination of the reagents. This makes frequent changing of the reagents necessary.

The Leica TP 1020 is a tissue processor with several process chambers that are arranged in a circle. The reagents for the tissue samples are contained in the process chambers. Two wax-filled chambers, which can be heated, are also provided for. The mechanism for changing the tissue samples is disclosed in German Patent DE 196 47 662. A mechanism to drive the tissue processor that processes samples for histological examination is provided for beneath the process chambers. A centrally located guide rod is moved by means of a toothed belt. The guide rod may be raised or lowered by a movement of the toothed belt via the drive mechanism. A carrousel is attached to the upper area of the guide rod, which has several object holders that are introduced into one of the process chambers. Each of the object holders has a lid with a circumferential seal. After the holder is introduced into one of the process chambers, they are rendered completely airtight by the seal.

The underlying problem of the invention is to create a device in which small tissue samples (biopsies) can be prepared quickly and economically for histological preparation. In the process, the risks associated with the reagents used are to be substantially reduced.

This problem is resolved by a device with the features described in the characterizing part of claim 1.

A further problem of the invention is to develop a method by which small tissue samples (biopsies) can be processed quickly and economically for histological preparation.

This problem is resolved by a method that is characterized by the steps in claim 14.

It is of advantage for the process of desiccation and infiltration with paraffin of small volumes of tissue sample (such as biopsies) to be reduced to only a few steps with a short dwell time. An example would be a dwell time of 30 seconds in ethanol; a dwell time of 6 minutes in acetone; and a dwell time of 6 minutes in paraffin. Here, the entire process takes 12.5 minutes. Because this process must be started several times per day for urgent testing, a capacity of 20 cassettes is suitable. A small table device should allow for these circumstances. In order to optimize desiccation in spite of the short dwell time, the reagents (ethanol and acetone) are exchanged via a reservoir, in contrast to known tissue processors. This reservoir has many times the volume of the process chambers that contain the preparations. This circumstance has several advantages. In spite of the small size of the process chamber, a large volume of liquid is available. The process chamber can be emptied and refilled with fresh reagent during the process. A certain number of processes can be carried out with supply from a freshly filled reservoir, without having to refill it with fresh reagent. This is also the case when the used reagent is pumped back into the reservoir.

Emptying the process chamber after each step of the process has been concluded also has the advantage that all the reagent, which is usually a volatile solvent, is back in the reservoir. The solvents that are used pose a certain safety risk (flammability, fumes). This emptying also reduces the handling of these solvents.

The device is advantageously fitted with a housing that is divided by a baseplate into an upper part and a lower part. Several process chambers are arranged on the baseplate, and a transport mechanism transfers the tissue samples into the process chambers. The process chamber itself has a first opening through which the process chamber may be filled or emptied. Several reservoirs containing reagent are provided for in the housing beneath the baseplate, such that the reagent may be pumped from one of the reservoirs into the process chamber and from the process chamber back into that reservoir.

The process chambers are designed in the form of cups, each of which has a side wall and a floor, such that the first opening and the second opening are in the floor of the process chamber. This is an advantage because the tubing that feeds the process chambers with reagent leads directly from the floor of the process chamber in the bottom part of the device. As a result, there is no clutter of tubing in the upper part of the device.

The transport mechanism is fitted with a transport arm to which is attached a holder for several cassettes with histological tissue samples. A lid is attached to the holder, which closes the process chamber when the process chamber is in the lowered holder. The lid has a certain freedom of movement, which, when the holder is shaken, allows it to remain seated on the process chamber.

Figure 2:
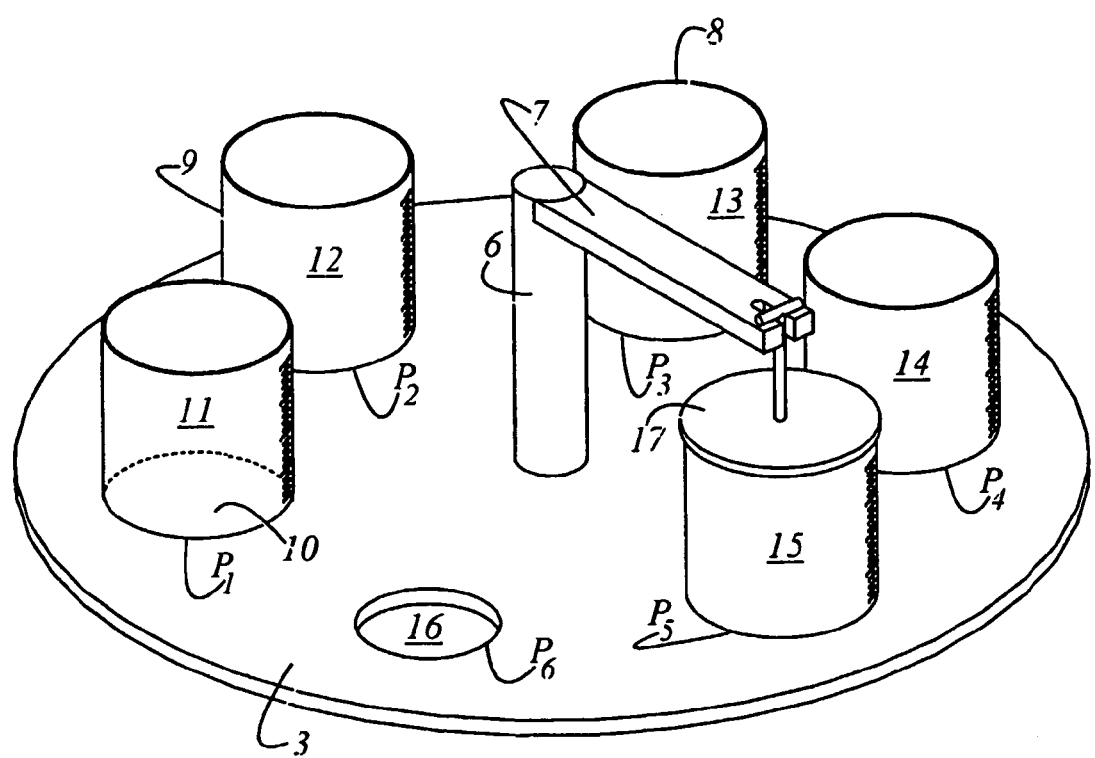

The subject of the invention is schematically depicted in the diagram, and will be described in the following figures. They show:

FIG. 1 a schematic diagram of the arrangement of the process chambers on the baseplate inside the device;

FIG. 2 a schematic diagram of the arrangement of the process chambers, showing the tissue carriers lowered into the last process chamber.

Figure 3:
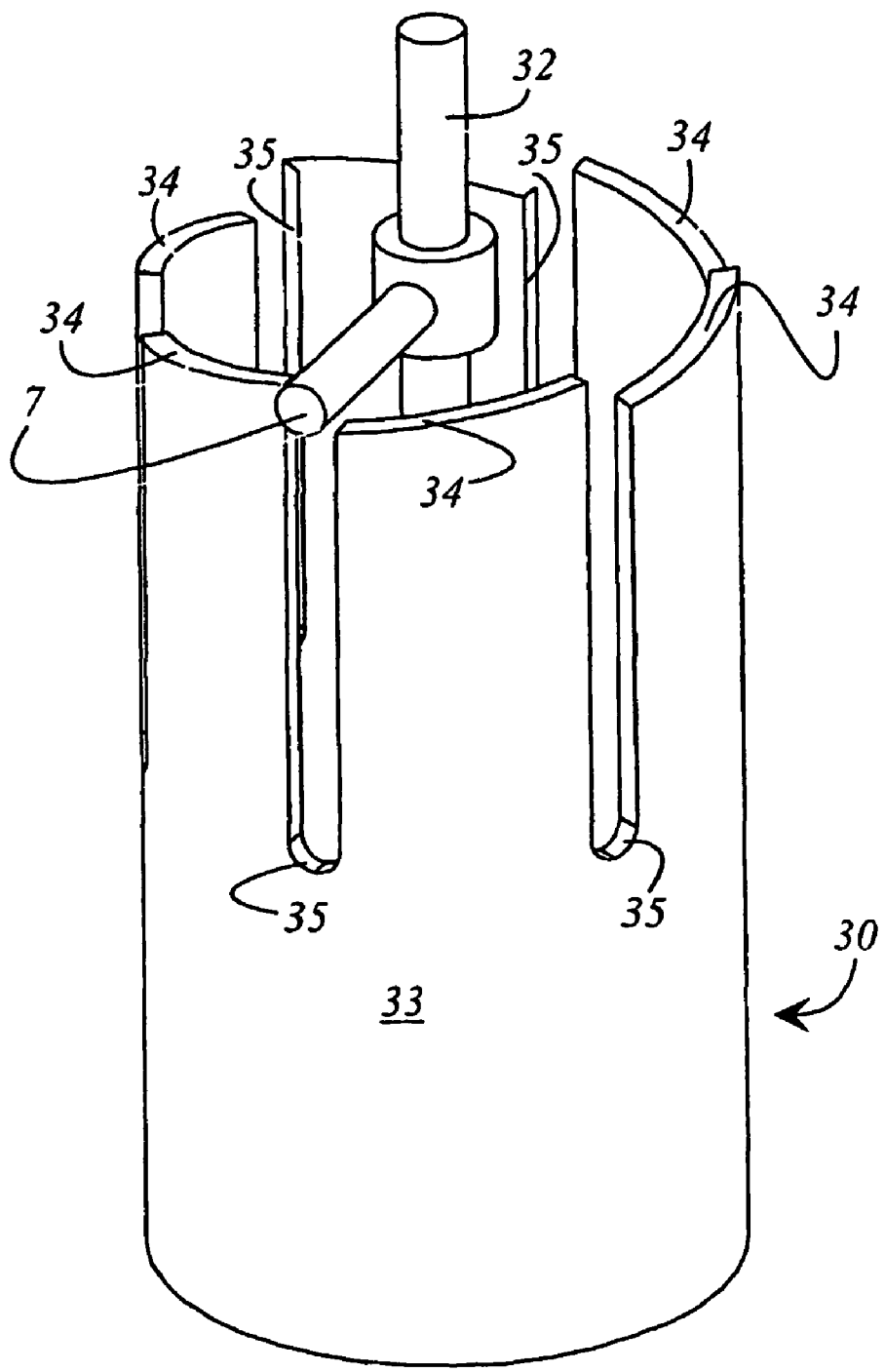
Figure 4:
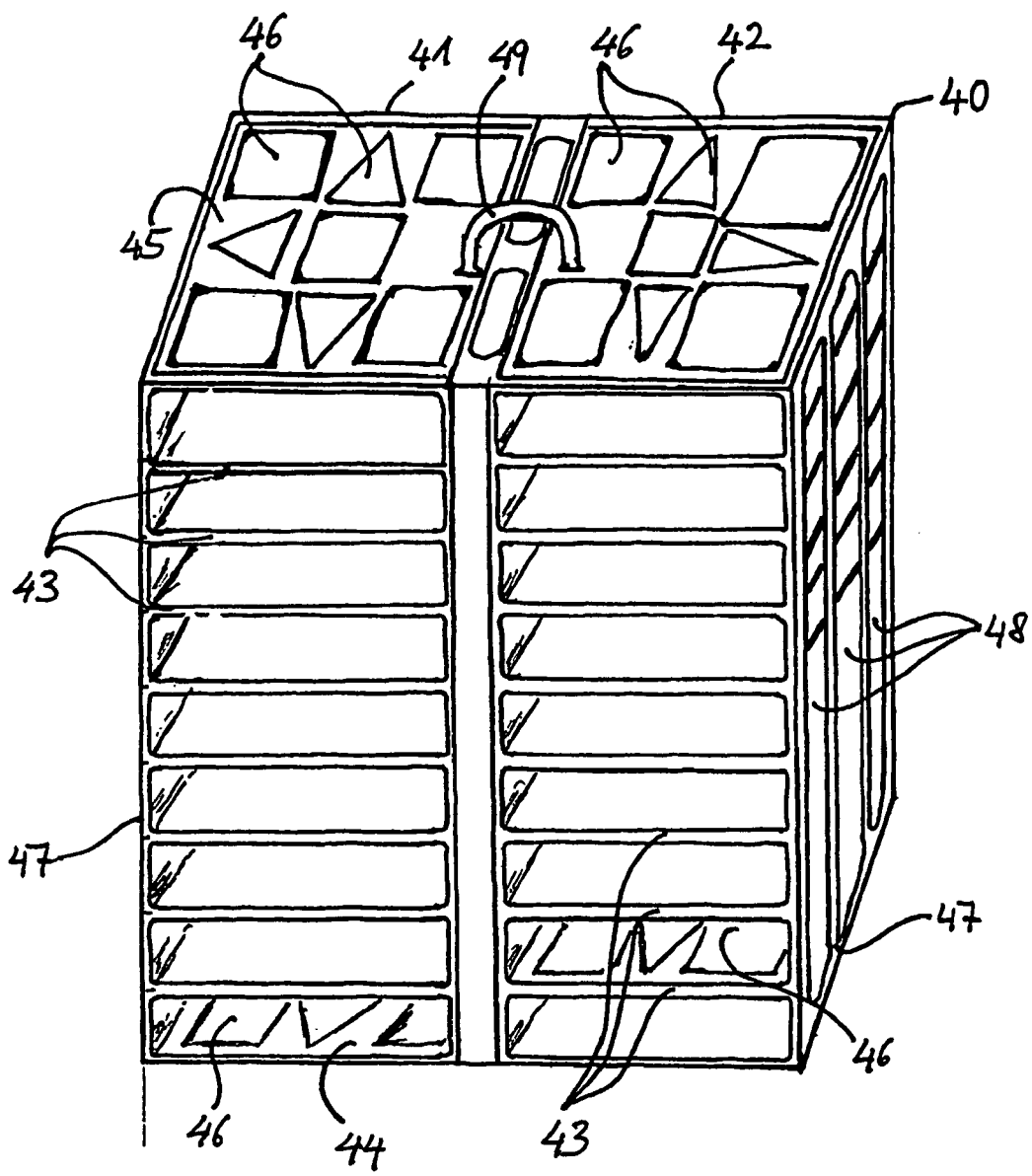
Figure 5:
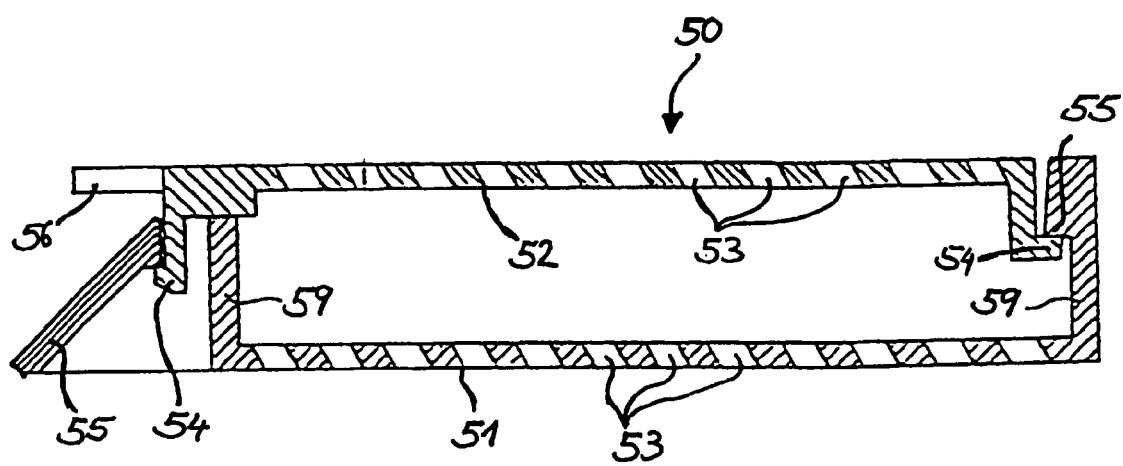
Figure 6:
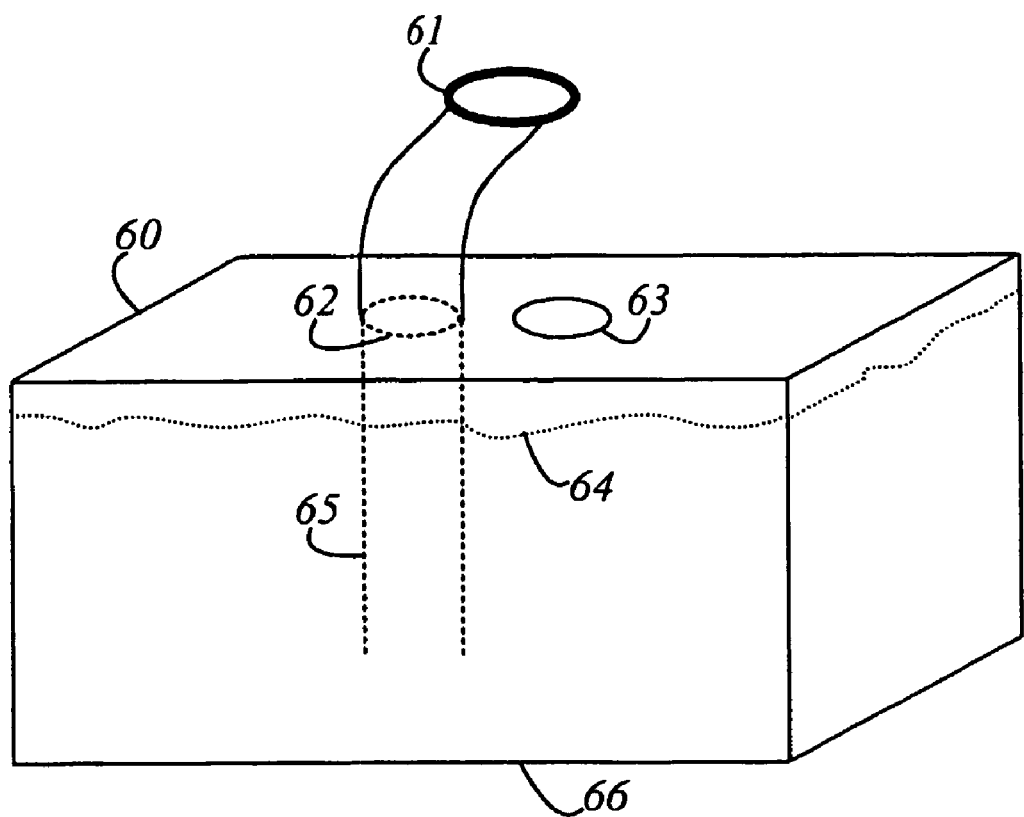
Figure 7:
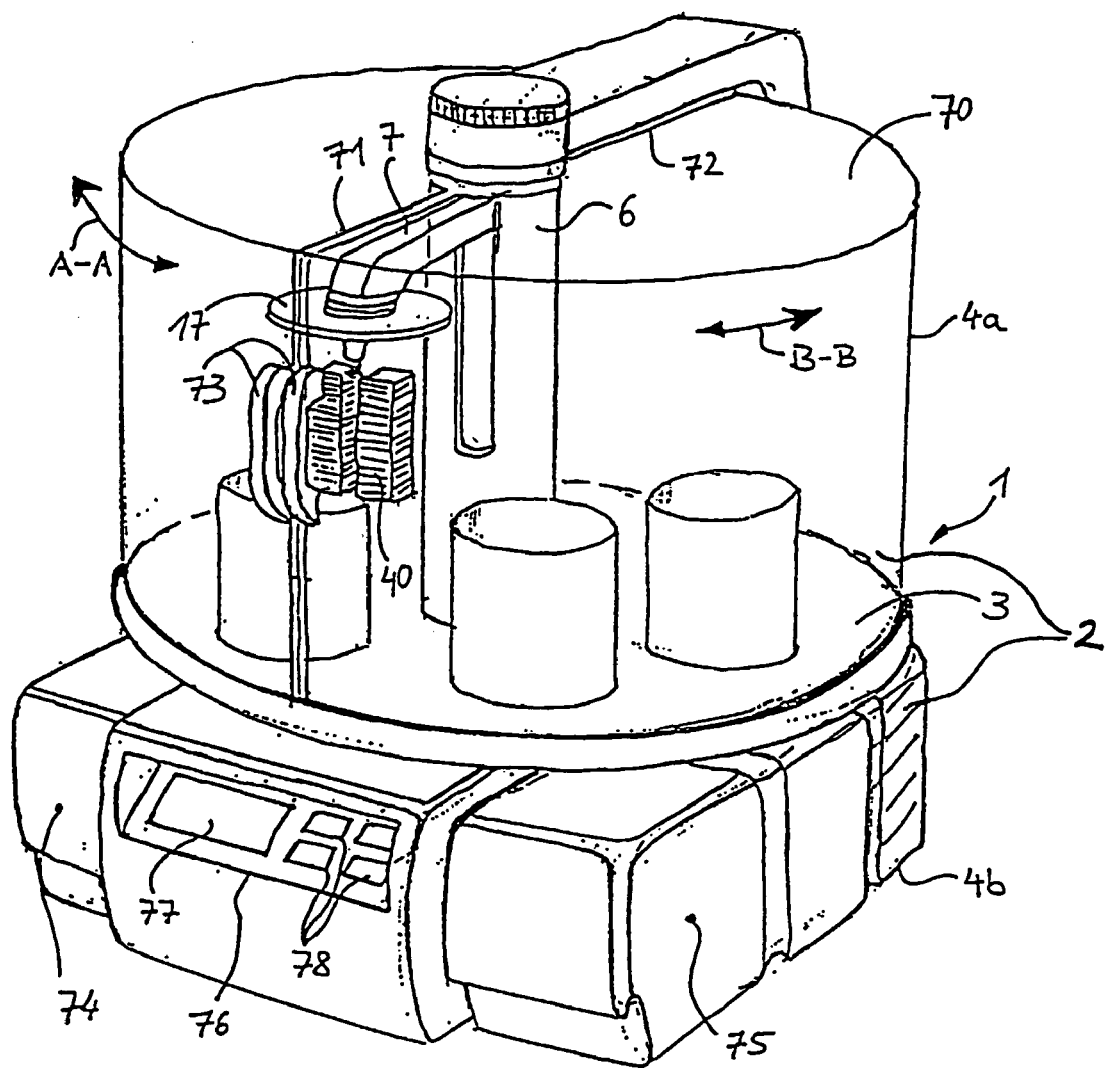

FIG. 3 the drive and movement mechanism to raise and lower the holder with the tissue carriers into and out of the process chamber;

FIG. 4 a schematic perspective diagram of the holder;

FIG. 5 a lateral view of a cassette for receiving histological tissue samples;

FIG. 6 a schematic perspective diagram of a reservoir;

FIG. 7 a perspective diagram of the device; and

Figure 8:
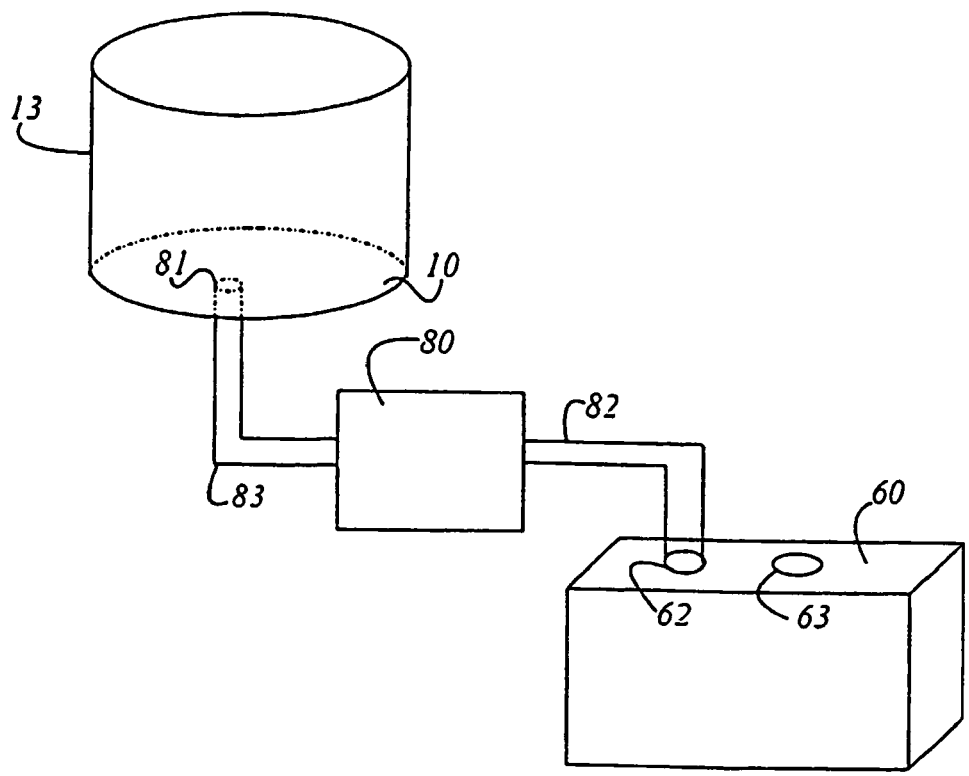
Figure 9:
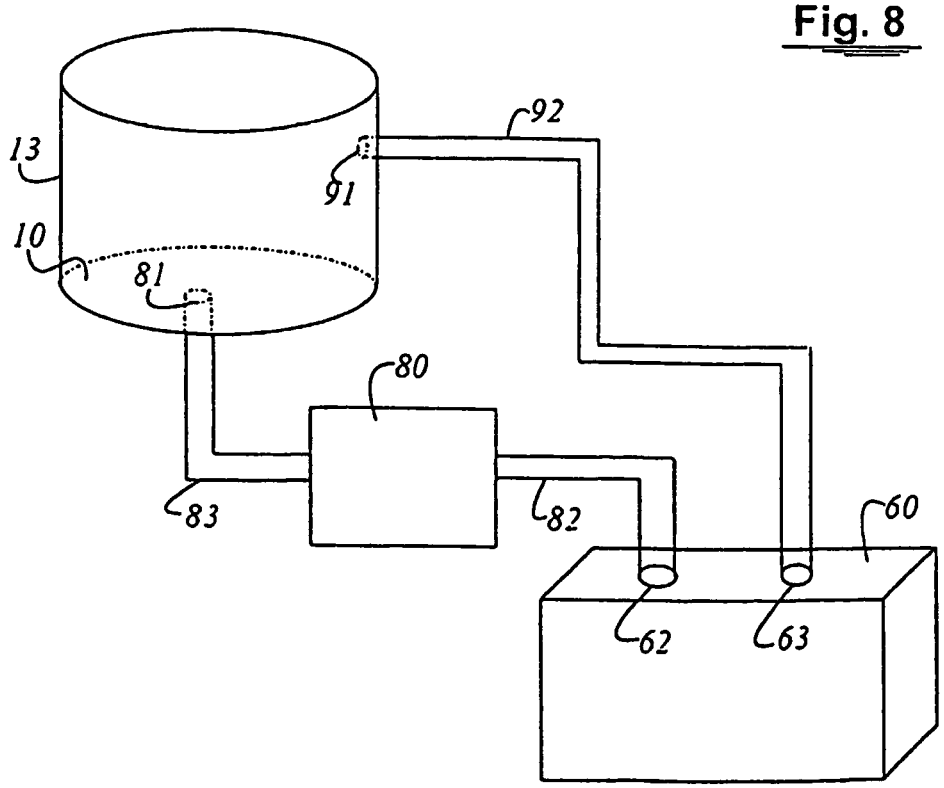

FIG. 8 a schematic diagram of a process chamber connected to the pump and a reservoir; and FIG. 9 a further development of the arrangement of process chambers, pump, and reservoir, in which the process chamber exhibits two openings.

An arrangement of several process chambers (11, 12, 13, 14, and 15) on a baseplate (3) is shown in FIG. 1 and FIG. 2. A schematic perspective of the entire device (1) for the fast processing of tissue samples for histological examination is shown in FIG. 7. In the embodiment depicted in FIG. 1, the process chambers are labeled 11, 12, 13, 14, and 15. A linear arrangement of the process chambers is also conceivable. A device (1) for the fast processing of tissue samples for histological examination consists of a housing (2), which the baseplate (3) separates into an upper part (4a) and a lower part (4b). The following description is limited to a circular arrangement of the process chambers (11, 12, 13, 14, and 15). However, this should not be viewed as a limitation of the invention.

In the center (5) of the baseplate (3), a transport mechanism (6) with a transport arm (7) are provided for in the housing (2) of the device (1). The device (1) is designed to carry out a process of desiccation and subsequent infiltration with paraffin (wax) of small sample volumes. Small sample volumes such as biopsies are placed in the process chambers (11, 12, 13, 14, and 15) of the device (1) so the water may be withdrawn from them using various solvents. Replacement of this water (tissue fluid) is then done in other process chambers using paraffin (wax). These process chambers are designed to be heatable. The tissue samples themselves are placed in special cassettes (50, see FIG. 5). Several cassettes (50) are used in a common holder (40), which is lowered into or lifted out of the various process chambers by means of the transport mechanism (6). There is room for approximately 20 cassettes (50) in the holder (40), which can be manufactured out of, among other things, plastic. The plastic manufacture of the holder (40) allows it to be for single-use. Once the process has run its course, that is, the tissue sample has been desiccated and the water replaced with paraffin, the holder (40) does not need to be cleaned for the next round of processing. The used holder is disposed of or recycled. A new holder (40) is used for each round of processing.

To transport the holder (40) from one process chamber to the next process chamber, a relative motion is generated between the transport mechanism (6) and the baseplate (3). In the embodiment described here, the baseplate (3) is stationary and the transport mechanism (6) moves from process chamber to process chamber.

In the embodiment depicted in FIG. 1 and FIG. 2, six positions ($P_1$, $P_2$, $P_3$, $P_4$, $P_5$, and $P_6$) are provided for, of which five positions ($P_1$, $P_2$, $P_3$, $P_4$, and $P_5$) are each fitted with a process chamber. Each process chamber is in the form of a cup (8) that has a cylindrical side wall (9) that is closed on one side by a floor (10). The process chamber itself may have either one or two openings. In process chambers that have one opening, filling and emptying occur through this one opening, which runs into the floor (10) of the process chamber. In process chambers with two openings, a constant irrigation of the process chamber with solvent is possible. Good irrigation is achieved when one opening is situated on the floor and the second opening at the top of the fluid level in the process chamber. In the device according to the invention, filling, emptying, and irrigation are done only in those process chambers into which solvent is to be introduced.

In the embodiment depicted in FIG. 1, the first process chamber (11) is provided for in position $P_1$. This first process chamber (11) represents the loading position of the device (1). For example, a holder (40) with cassettes (50) for histological processing can be placed in the process chamber (11). A liquid suitable for medium-term storage and to prevent drying of the tissue samples is contained in the first process chamber (11). The liquid (fixans) in the first process chamber (11) may be formaldehyde, for example. A second process chamber (12) follows the first process chamber (11) in position $P_2$. The holder (40) is raised somewhat and attached to the transport arm (7) of the transport mechanism (6), which is situated above the first process chamber (11). When the process starts, the transport arm (7) lifts the holder (40) and lowers it into the second process chamber (12). In the meantime the holder (40) is transferred to the second process chamber (12), and liquid is introduced into the second process chamber (12) through an opening in the second process chamber (12). The liquid used is ethanol. Filling should be done quickly in order to prevent drying of the tissue samples. While the holder (40) is in the second process chamber (12), the holder (40) is moved up and down (agitated) to optimize irrigation of the tissue samples with liquid. The holder (40) remains in the second process chamber (12) for time $t_1$. Time $t_1$ in the process chamber (12), which is filled with ethanol, should not exceed 30 seconds.

A third process chamber (13) follows the second process chamber (12) in position $P_3$. The holder (40) is lifted out of the second process chamber (12) with the transport arm (7) attached to the transport mechanism (6), and transported to the third process chamber (13). While the holder (40) is transferred to the third process chamber (13), liquid is introduced into the third process chamber (13) through an opening in the floor (10) of the third process chamber (13). The liquid used is acetone. The second process chamber (12) is emptied in parallel during this time. At the least, the second and third process chambers (12 and 13) are fitted with one fluid pump each (not depicted). The directionality of the fluid pumps is reversible. As a result, liquid can be pumped into and out of a process chamber without the necessity of valves. The holder (40) remains in the third process chamber (13) for a time, $t_2$, such that time $t_2$ does not exceed six minutes.

A fourth process chamber (14) that is filled with wax is provided for in position $P_4$. A fifth process chamber (15) that is also filled with wax is provided for in position $P_5$. Two wax baths (wax-filled process chambers) are commonly used, because the wax in the fourth process chamber (14), which is the first wax bath, generally becomes contaminated by solvent residue. At least one wax-filled process chamber contains no opening and is heatable. The wax chambers (two units are appropriate) must be filled manually. The holder (40) remains in one of the filled process chambers (14 and 15) for time $t_3$. Time $t_3$ in the wax-filled process chambers (14 and 15) should not exceed six minutes. However, it is conceivable to use only one wax-filled process chamber. In that case, the holder (40) remains in the single wax-filled process chamber for time $t_3$.

Position $P_6$ is empty and is designed as an unloading station. The operator can remove the holder (40) along with the prepared tissue samples from the device (1). Position $P_6$ is fitted with a drip pan (16) for removing the preparation holder. For example, the transport arm (7) of the transport mechanism (6) removes the holder (40) from the fifth process chamber (15) and sets it on the drip pan (16). FIG. 2 depicts the situation in which the holder has been lowered into the fifth wax-filled process chamber (15). The fifth process chamber (15) is closed with a lid (17). The lid (17) is attached to the transport arm (7) of the transport mechanism (6) above the holder (40) which, as shown in FIG. 2, closes the process chamber into which the holder (40) is lowered.

FIG. 3 shows the drive and motion mechanism (30) for lifting and lowering the holder (40) with the tissue carriers into the process chambers. The rest of the description relates to the device (1) with a circular arrangement of process chambers. The drive and motion mechanism (30) consists of a spindle (32) which serves to lift and lower the transport arm (7). In the case of the central arrangement of the transport mechanism (6), a steering mechanism (33) is provided for around the spindle (32), which exhibits beveled surfaces (34) corresponding to the number of process chambers. The beveled surfaces (34) are each interrupted by gaps (35). When the transport arm (7) is completely lifted by the spindle (32), that is, the holder (40) has been completely lifted out of the process chamber, the transport arm interfaces with the surface (34). The transport arm (7) glides along the beveled surface (34) in the direction of a gap (35) solely as a result of gravity. The transport arm then drops through the gap (35) into the process chamber.

FIG. 4 shows a schematic perspective of a holder (40) for cassettes (see FIG. 5). The holder consists of a first and a second rectangular part (41 and 42), which are both firmly attached to each other. Both the first and the second part (41 and 42) contain numerous shelves (43) that are suitable for receiving cassettes. There are openings (46) in both the floor (44) and the top cover (45) of the holder (40), as well as in the individual shelves (43), which are designed for good irrigation of the holder (40) with reagent. Openings (48) in the side walls (47) of the holder (40) serve the same purpose. A bracket (49) is attached to the top cover of the holder (40), which the transport arm (7) of the transport mechanism (6) can grab hold of.

FIG. 5 is a lateral view of a cassette (50) for receiving a histological tissue sample and then processing it with the appropriate liquids. The cassettes (50) can be used in the holder (40) shown in FIG. 4. The cassette (50) consists of a floor (51) with attached side parts (59); the cassette (50) can be closed with a detachable top cover (52). There are numerous slits (53) in both the floor (51) and in the top cover (52) that ensure irrigation of the entire cassette (50) with liquid. The top cover (52) has several clasps (54) that engage with other clasps (55) that are arranged along the side parts (59) and the floor (51). For better handling when opening and/or closing, brackets (56) are provided for on the top cover (52).

FIG. 6 is a schematic perspective diagram of an embodiment of a reservoir (60). The coupling of the reservoir (60) to the device (1) is achieved by means of a plug connector (61). The first reservoir opening (62) and second reservoir opening (63) in the reservoir (60) are located above the fluid level (64). The first reservoir opening (62) is the outflow of a channel (65) that reaches all the way to the floor (66) of the reservoir (60). The second reservoir opening (63) sticks out of in a part of the device (1) that is attached to suction. Fumes that develop, particularly when pumping the liquid back into the reservoir (60), are thus sucked out. When docking the reservoir (60) to the lower part (4b) of the device (1), the reservoir opening (62) is tightly connected to the pump via an O-ring (not depicted).

FIG. 7 again shows the entire device (1) in perspective. The upper part (4a) of the device (1) is covered by a transparent hood (70). The hood (70) is set around the central transport mechanism (6) and consists of a first part (71) and a second part (72) that may be opened and closed around the central transport mechanism (6). The directionality of opening and closing is indicated by the double arrows A-A and B-B. For opening or closing, a latch (73) is attached to both the first part (71) and to the second part (72). Under the transparent hood (70), which is made of plastic, may be seen the individual process chambers, the transport arm (7) with the holder (40) for the cassettes (50), and the transport mechanism (6). A fan with an activated charcoal filter (not depicted), which draws off solvent fumes from the area of the hood (70) and directs it to an exhaust (not depicted) by means of a hose (not depicted), is integrated into the device (1). The hood (70) covers almost the entire baseplate (3) and the upper part (4a) of the device (1). A first reservoir (74) and a second reservoir (75) for the solvents used in the device (1) are each integrated laterally into device in the lower part (4b). The solvents may, for example, be ethanol and acetone. The first reservoir (74) and the second reservoir (75) may be removed for refilling or to replenish the used solvent. At the front of the device, an operating panel (76) to start the program that runs the device (1) is depicted schematically. The operating panel (76) has a display (77) and several operator controls (78) by which the processing of tissue samples may be individually programmed. In addition, the following undepicted elements are included in the area between the first reservoir (74) and the second reservoir (75) in the lower part (4b) of the device: two fluid pumps, the fan, the electrical drive mechanism for the transport mechanism (6), a power source, and a controller.

FIG. 8 shows a schematic diagram of a process chamber (13) connected to a pump (80) and a reservoir (60). A first tube (82) leads from the first reservoir opening (62) to the pump (80), and a second tube (83) leads from the pump (80) to a first opening (81) in the floor (10) of the process chamber (13). The directionality of the pump (80) is reversible. Because of this, only one pump is needed to fill or empty the process chamber (13).

A further embodiment of the system consisting of a process chamber (13), a reservoir (60), and a pump (80) is depicted in FIG. 9. A first tube (82) leads from the first reservoir opening (62) to the pump (80), and a second tube (83) from the pump (80) to an opening (81) in the floor (10) of the process chamber (13). There is a second opening (91) in the process chamber (13) that is connected with a third tube (92). The second opening (91) may also the set in the floor (10) of the process chamber (13). The third tube (92) terminates at the second reservoir opening (63). This development makes it possible to continuously circulate the reagent between the reservoir (60) and the process chamber (13).

The invention claimed is:

1. A device for processing tissue samples for histological examination, comprising:
   a housing comprising an upper part and a lower part divided by a baseplate;
   several process chambers, each process chamber comprising a side wall and a floor, the process chambers being arranged on the baseplate and capable of being filled with a reagent;
   a transport mechanism, transferring the tissue samples to the process chambers, the transport mechanism comprising a transport arm and a holder for several cassettes for tissue samples attached to a transport arm; and
   a drive mechanism attached to the transport arm and causing a relative rotational motion between the transport mechanism and the baseplate,
   wherein the rotational motion causes the transfer of the tissue samples between the process chambers;
   wherein the process chambers are arranged around the axis of the rotational motion;
   wherein the transport arm is lowered by gravity introducing the holder into the process chamber;
   wherein at least one process chamber comprises a first opening in the floor; and wherein the process chamber may be filled with a reagent or emptied of a reagent through the first opening simultaneously with the transferring.

2. The device according to claim 1, further comprising a lid attached to the top of the holder, wherein the lid closes the process chamber when the holder is lowered into the process chamber.

3. The device according to claim 2, wherein the lid has a freedom of movement, so that, when the holder is shaken in the process chamber by the transport mechanism, the lid remains seated on the process chamber.

4. The device according to claim 1, wherein at least one process chamber comprises a second opening, wherein the second opening in combination with the first opening allows continuous pumping of a reagent through the process chamber.

5. The device according to claim 1, wherein at least one process chamber has no openings in either its side wall or its floor and is heatable.

6. The device according to claim 1, wherein at least one process chamber has no openings in either its side wall or its floor and is capable of being manually filled with wax.

7. The device according to claim 1, wherein the process chambers are cup-shaped, and wherein at least one process chamber comprises the first opening and a second opening in the floor of the process chamber.

8. The device according to claim 7, wherein the volume of the process chambers is a multiple of the volume of a tissue sample contained in the holder.

9. The device according to claim 8, wherein the holder is manufactured out of plastic and is designed for single-use processing.

10. The device according to claim 1, further comprising several replaceable reservoirs for reagent positioned under the baseplate in the housing, wherein the reagent may be pumped from one of the reservoirs into one of the process chambers and from the process chamber back into that reservoir.

11. A method for processing of tissue samples in several process chambers, each of the process chambers comprising a side wall and a floor, comprising the following steps:
lowering a holder with cassettes for tissue samples into a loading position, comprising a first process chamber containing a reagent for intermediate storage of the tissue samples;
lifting of the holder by a transport arm attached to a transport mechanism;
transfer of the holder to a second process chamber;
filling simultaneously with the transfer the second process chamber through an opening in the floor of the second process chamber;
lowering of the holder into the second process chamber;
keeping the holder in the second process chamber for a time $t_1$;
removal of the holder from the second process chamber;
transfer of the holder to a third process chamber;
emptying simultaneously with the transfer the second process chamber;
filling simultaneously with the transfer the third process chamber; lowering of the holder into the third process chamber; keeping the holder in the third process chamber for a time $t_2$;
removal of the holder from the third process chamber;
emptying the third process chamber after the removal of the holder;
lowering of the holder into a first wax-filled process chamber;
keeping the holder in the wax-filled process chamber for a time $t_3$; and
lowering of the holder into an unloading station.

12. The method according to claim 11, wherein the time $t_1$ does not exceed 30 seconds and the second process chamber is filled with ethanol.

13. The method according to claim 11, wherein the time $t_2$ does not exceed 6 minutes and the third process chamber is filled with acetone.

14. The method according to claim 11, wherein the time $t_3$ does not exceed 6 minutes.

15. The method according to claim 14 further comprising a second wax-filled process chamber used after the first wax-filled process chamber to reduce transfer and contamination with a solvent.

16. The method according to claim 11, wherein the process chambers are filled and emptied from and into replaceable reservoirs in a lower part of a housing separated from an upper part of the housing by a baseplate.

17. The method according to claim 11, characterized wherein a relative movement is generated between the process chambers and a transport arm to transfer the holder from one process chamber to another process chamber.

* * * * *